US005759562A

United States Patent [19]
Rhodes et al.

[11] Patent Number: 5,759,562
[45] Date of Patent: Jun. 2, 1998

[54] COMPOSITIONS FOR CONTROL OF SOIL PESTS

[75] Inventors: David John Rhodes, Crowthorne; Jill Foundling, Finchampstead; Joanna Theresa Porter, Okehampton, all of United Kingdom

[73] Assignee: Zeneca Limited, London, England

[21] Appl. No.: 735,045

[22] Filed: Oct. 22, 1996

Related U.S. Application Data

[63] Continuation of Ser. No. 366,176, Dec. 29, 1994, abandoned.

[30] Foreign Application Priority Data

Dec. 29, 1993 [GB] United Kingdom ............ 9326517

[51] Int. Cl.$^6$ ............................................. A01N 25/12
[52] U.S. Cl. ................... 424/409; 424/93.5; 424/405; 424/408; 424/410; 424/418; 424/421; 424/489
[58] Field of Search ............................ 424/489, 405, 424/93.5, 408, 410, 411, 418–421, 409; 71/64.05, 64.13

[56] References Cited

U.S. PATENT DOCUMENTS

| 4,626,508 | 12/1986 | Steinkraus | 435/832 |
|---|---|---|---|
| 4,713,342 | 12/1987 | Chet et al. | D71/3 |
| 4,824,671 | 4/1989 | Ellis et al. | 435/832 |
| 4,886,664 | 12/1989 | Jung et al. | 435/252.2 |
| 4,921,703 | 5/1990 | Higuchi et al. | 424/409 |
| 4,925,663 | 5/1990 | Stimac | 435/911 |
| 5,055,293 | 10/1991 | Aronson et al. | 424/93 |
| 5,068,105 | 11/1991 | Lewis et al. | 435/932 |
| 5,141,744 | 8/1992 | Chang et al. | 424/93 |
| 5,189,831 | 3/1993 | Miller et al. | 424/405 |
| 5,238,681 | 8/1993 | Chang et al. | 424/405 |
| 5,288,296 | 2/1994 | McCabe et al. | 435/822 |

FOREIGN PATENT DOCUMENTS

| 0 097 571 | 1/1984 | European Pat. Off. . |
|---|---|---|
| 0 250 908 | 1/1988 | European Pat. Off. . |
| 0 268 177 | 5/1988 | European Pat. Off. . |
| 0 286 351 | 10/1988 | European Pat. Off. . |
| 0 314 439 | 5/1989 | European Pat. Off. . |
| 0 387 640 | 9/1990 | European Pat. Off. . |
| 0 406 103 | 1/1991 | European Pat. Off. . |
| 0 494 592 | 7/1992 | European Pat. Off. . |
| 0 543 438 | 5/1993 | European Pat. Off. . |
| 2202159 | 5/1974 | France . |
| 298 038 | 2/1992 | Germany . |
| 59082085 | 5/1984 | Japan . |
| 05084064 | 4/1993 | Japan . |
| 84/01089 | 3/1984 | WIPO . |
| 92/08355 | 5/1992 | WIPO . |

OTHER PUBLICATIONS

Keller, S. and Zimmerman, G.; "Mycopathogens of Soil Insects," Insect–Fungus Interactions, pp. 239–270 (1989).

Barlett, M.C. and Jaronski, S.T., "Mass production of entomogenous fungi for biological control of insects," Burge. Fungi in Biological Control Systems, pp. 61–85 (1988).

Andersch, W. "Production of fungi as crop protection agents," Pflanzenschutz–Nachrichten Bayer, 45/1992, pp. 129–142.

Blachere, H., Calvez, J., Ferron, P., Corrieu, G. and Peringer, P., "Studies of the Formulation and Conservation of an Entomopathogenous Preparation of Blastosopres of *Beauveria tenella*," Ann. Zool. –Ecol. anim., 5(I), pp. 69–79 (1973).

Fargues, J., Robert P. H. and Reisinger, O., "Formulation Aspects for Large–scale Productions of the Entomopathogenic Hyphomycete Beauveria for Field Applications," Ann. Zool. –Ecol. anim., 11(2), pp. 247–257 (1979).

Shasha, B.S. and McGuire, M.R., "Method and Compositions of Adherent Starch Granules for Encapsulating Pest Control Agents," U.S. Agricultural Research Service Report No. PAT–APPL–7–730 763 (Publication of U.S. Patent Appln. Serial No. 07/730,763, filed Jul. 16, 1991).

Fargues, J., Reisinger, O., Robert, P.H. and Aubart, C., "Biodegradation of Entomopathogenic Hyphomycetes: Influence of Clay Coating on *Beauveria bassiana* Blastospore Survival in Soil," Journal of Invertebrate Pathology, 41, pp. 131–142 (1983).

Ward, Michael G., "Formulation of Biological Insecticides," Advances in Pesticide Formulation Technology, pp. 175–184 (1984).

Lewis, J.A. and G.C. Papavizas, "Application of Trichoderma and Gliocladium in alginate pellets for control of Rhizoctonia damping–off," Plant Pathology, 36, pp. 438–446 (1987).

Knudsen, G.R. and Bin, Li, "Effects of Temperature, Soil Moisture, and Wheat Bran on Growth of *Trichoderma harzianum* from Alginate Pellets," Phytopathology, vol. 80, No. 8, pp. 724–727 (1990).

Rhodes, D.J., "Formulation requirements for biological control agents," Aspects of Applied Biology, 24, pp. 145–153 (1990).

*Primary Examiner*—Neil S. Levy
*Attorney, Agent, or Firm*—Melissa A. Shaw

[57] ABSTRACT

A granular composition comprising a pesticidally active amount of a fungal biological control agent said agent being present in the form of blastospores.

3 Claims, No Drawings

COMPOSITIONS FOR CONTROL OF SOIL PESTS

This application is a continuation of application Ser. No. 08/366,176, filed Dec. 29, 1994, now abandoned.

This invention relates to improved compositions for controlling soil pests, particularly insect pests, said composition comprising a biological control agent.

Soil pests, such as rootworms, wireworms, root flies and nematodes result in serious losses of yield in many of the world's major crops. In some cases, satisfactory control is achieved by means of chemical crop protection agents, but a number of major products for soil pest control are threatened with restriction or withdrawal by regulatory authorities. The development of biological control agents against soil pests would therefore be a desirable goal.

Probably the most significant technical hurdle to be overcome in the development of biological control agents is formulation. Few formulations of biological control agents, with the exception of *Bacillus thuringiensis*—based products, are presently capable of satisfying the requirements of efficacy, shelf life, and low production cost (Rhodes, 1990. *Aspects of Applied Biology* 24: 145–153).

This is particularly so in the case of fungi which are used for control of soil pests. To date, very few such products are available, and formulations which have been tested in the field have, in general, been based on simple semi-solid fermentation approaches such as application of colonised cereal grains (Keller & Zimmermann, 1989. Pp. 239–270 in Wilding et al. Insect-Fungus Interactions. Academic Press, London). An alternative approach is that described by Andersch et al., 1990. EP87 116–508, in which the fungus is grown in liquid culture as mycelial pellets which are then dehydrated and applied to soil. A similar approach, using hyphal fragments, is that described verbally by Krueger & Roberts (Society for Invertebrate Pathology Annual Meeting, 1988, using the technology described in WO 84/01089).

Submerged fermentation of fungal biomass in liquid culture is desirable, since such production is compatible with existing industrial practice, and the cost of production is relatively low. When grown in liquid culture, many entomopathogenic fungi, such as the genera Beauveria, Verticillium, Nomuraea, Tolypocladium, Paecilomyces (Bartlett & Jaronski, 1988. Pp. 61–85 in Burge. Fungi in Biological Control Systems. Manchester University Press, Manchester) and Metarhizium (Andersch, 1992. *Pflanzenschutz-Nachricten Bayer* 45: 129–142) produce yeast-like blastospores. Unfortunately, these are delicate structures, and difficult to formulate (Andersch, vide supra).

There are few descriptions of successful formulation of blastospores. Blachère et al., 1973. *Ann. Zool. Écol. anim.* 5: 69–79 described a means of preserving blastospores of *Beauveria tenella* by desiccation on silica powder, but this contained no nutrients designed to stimulate fungal growth in soil, and yielded a dusty material unsuitable for granular application to soil. In addition, the drying process (drying for 5 to 36 hours in a ventilated oven) would be impractical on an industrial scale. Fargues et al., 1979. *Ann. Zool. Écol. anim.* 11: 247–257 attempted to formulate blastospores of Beauveria species. Although such formulations maintained viability for eight months under refrigeration, the material lost infectivity over a five month period, even when stored at 5° C.

The property of certain clays in extending the viability of blastospores in soil was discussed by Fargues et al., 1983. *J Invert. Pathol.* 41. 131–142. However, this did not result in the production of an agronomically useful formulation. Selection of particular clays for formulation of entomopathogenic fungal propagules was alluded to by Ward, 1984. Pp. 175–184 in Scher. Advances in Pesticide Formulation Technology. ACS. Washington DC.

Formulation of fungi for application to the soil has been described in the case of non-blastospore-forming fungi which are used for purposes other than pest control. For example, the incorporation of fungi of the genera Trichoderma and Gliocladium into granules was described by Lewis & Papavizas, 1987. *Plant Pathology* 36: 438–446, by means of alginate encapsulation. Knudsen & Lin, 1990. *Phytopathology* 80: 724–727 incorporated nutrients into similar formulations of these fungi. Addition of nutrients increased hyphal density in the region of the granule, but did not increase the distance over which hyphae extended into the soil.

It may be seen, therefore, that the invention of an agronomically useful formulation which incorporates blastospores of fungi pathogenic to soil pests, and which allows such fungi to grow and sporulate in the soil, would have considerable value for biological control of such pests.

Accordingly the present invention provides a granular composition comprising a pesticidally active amount of fungal biological control agent said agent being present in the form of blastospores.

Such granular formulations of fungal blastospores may also comprise in addition to the blastospores, other components selected from mycelial fragments, a solid diluent or support (hereinafter called "a filler") and a complex nutrient source which allows the fungus to grow and sporulate after application. In addition, the granules may contain other materials such as preservatives, antioxidants, baits or attractants, and osmoregulants.

Fungal inoculum is produced by inoculating a liquid culture medium such as Sabouraud's Dextrose Broth with viable propagules, consisting of conidia, blastospores or mycelium, of a fungus such as a member of the genera Beauveria, Metarhizium, Paecilomyces, Nomuraea, Tolypocladium, Hirsutella or Verticillium. The culture medium is contained in a sterile vessel such as a flask or fermenter. The culture is then grown for several days under conditions suitable for growth of the fungus, after which the biomass, which consists of a mixture of blastospores and hyphal fragments, is harvested by centrifugation or filtration. Water may be further removed from the preparation, for example under pressure.

Fillers may be for example mineral clays such as kaolin (china clay), montmorillonite, diatomaceous earth, vermiculite, fullers earth, and the like.

Nutrient for use in the compositions may be vegetable based finely ground powders such as those listed in Example 6 below. The choice of nutrient will vary according to which fungal biological control agent is used in the composition.

Fillers and nutrients are mixed together in the required proportions, for example by blending, and are further mixed with the fungal biomass. The resulting mixture is blended until a homogeneous mixture is obtained. Water, preferably deionised water, is added to the mixture until the consistency is appropriate to allow the material to be extruded.

The paste is then extruded under pressure to form granules. The granules may be spheronised. The granules are dried, for example in a fluidised bed or under forced air, and are subsequently stored at ambient temperature until used, for example under vacuum, in a nitrogen atmosphere, or in the presence of a desiccant such as silica gel.

The granules may be applied to soil, or to plant surfaces such as the whorls of maize plants, after which the fungus grows by hyphal extension before sporulating, increasing the probability that the fungus will encounter a susceptible host.

In a further aspect the invention provides a method of combating soil dwelling pests which are susceptible to the action of a fungal biological control agent which comprises applying to the soil a granular composition according to the invention.

EXAMPLE 1

Erlenmeyer flasks of volume 250 ml, containing 50 ml of Sabouraud's Dextrose Broth were inoculated, using a sterile loop, with conidia of a strain of the entomopathogenic fungus *Beauveria bassiana* which had previously been shown to be pathogenic to the banded cucumber beetle *Diabrotica balteata*. The flask was placed on an orbital shaker set at 200 rpm, and shaken at a temperature of 24° C. for a period of 7 days, after which the culture consisted of a mixture of blastospores and mycelial fragments, approximately 95% of which consisted of blastospores.

The biomass was centrifuged at 5000 rpm on a Sorvall RC3C swinging bucket rotor for 10 minutes, after which it was resuspended and re-centrifuged twice in sterile distilled water. Excess liquid was removed by squeezing the pellet between several layers of paper towelling, to a final moisture content of 75–85%.

A clay mixture was prepared consisting of GTY powder (kaolin) and Fulgel (fuller's earth) mixed in a pestle and mortar in a 14:5 ratio by weight. This was then ground together with the blastospore/mycelial fragment mixture in the ratio 83:17 by weight. Deionised water was added to the mixture in the approximate ratio 1:5 by weight until the paste reached a consistency suitable for extrusion. The paste was extruded under pressure through a 0.5 mm diameter Endecott sieve.

The granules were spheronised and dried for 25 minutes on a fluid bed dryer at ambient temperature, and subsequently stored in a vacuum-sealed desiccator in the presence of silica gel.

The viability of the granules was determined by homogenising the granules in 0.05% Tween 80 and plating the suspension on to Sabouraud's Dextrose Agar containing 0.05 g/l chloramphenicol. Surprisingly, the granules were found to retain viability after drying, $2 \times 10^7$ colony forming units (cfu)/g being recovered. Tween 80 is a registered trademark for a surfactant comprising polyoxyethylene (20) sorbitan monooleate.

EXAMPLE 2

Fungal biomass was produced as above by growing the fungus for six days in 1 litre Erlenmeyer flasks containing 500 ml of culture broth. Granules were prepared as in Example 1, except that a nutrient source was provided by mixing the clay mixture and fungal biomass with the nutrient in the ratio of 50:33:17 clay mixture:nutrient:fungal biomass by weight before preparing the paste for extrusion. The granules were air-dried for approximately 16 hours in a fume hood.

Colonisation of soil was determined by placing 1 g of dry granules between two 5 g layers of field soil at field capacity in a loosely capped plastic Universal container. Radial growth from the layer of granules was measured, and sporulation assessed visually after incubation for 18 days at 24° C. Results are shown in Table 1. The presence of a nutrient source, in particular soya flour, was shown to enhance growth and sporulation.

EXAMPLE 3

Extruded granules were prepared as in Example 2, both with and without nutrients (soya flour at 33%) and containing hyphal fragments or blastospores at the concentration of 1.7%, 10% or 17% by weight. Inoculum consisting primarily of blastospores was produced as descibed in Example 1. Inoculum consisting primarily of mycelium was produced by growing the fungus in the same medium and at the same temperature, but without shaking. The mycelium was then washed in deionised water, and homogenised to produce hyphal fragments before being collected by filtration on Whatman No. 1 filter paper.

The granules were added to soil, contained in plastic minipots, at the rate of 1% or 3% by weight. Soil moisture content was adjusted to 23%. Each of 8 pots was planted with a single germinated maize seed, and simultaneously infested with 10 1st instar larvae of *Diabrotica balteata* or *D. virgifera virgifera*. The pots were maintained at 20° C. for 10 days after which larval mortality was assessed. Results are shown in Table 2, indicating that mortality of both species was increased by the addition of a nutrient source, in this case soya flour, to the granules. Hyphae are denoted as Hy, blastspores as Bs.

EXAMPLE 4

Inoculum consisting primarily of blastospores was produced as described in Example 2, except that the fungus was grown in 1 litre flasks containing 400 ml culture medium. The inoculum was grown for either 4 or 7 days. Extruded granules were prepared as in Example 2. After extrusion, the granules were dried on a fluid bed dryer at 20° C. for between 8 and 30 minutes, except for the granules with a final moisture content of <3% which were dried for 16 minutes at 20° C. and 15 minutes at 30° C. The moisture content of the granules was determined, after which the granules were vacuum-sealed in bags and stored at ambient laboratory temperature (20°–25° C.) for six months. Results are shown in Table 3. Although the moisture content of the granules was found to have altered by the end of the experiment, despite the vacuum seal, it was evident that drying of the granules resulted in enhanced storage stability. There was some evidence that, in the case of the dry granules, stability was increased by growing the fungus for 7, instead of 4, days.

EXAMPLE 5

Extruded granules were prepared as in Example 4, containing 33% soya flour, 17% fungal biomass (grown for 3 days), 45% filler (GTY, Calflo E, Celite PF or Celite 500) and 5% binder (Fulgel, Borrebond or PEG 40000) by weight. Granules without binder contained 50% filler by weight. The granules were air-dried and then bioassayed against *Diabrotica balteata* as described in Example 3, except that the granules were incorporated into soil at 1% by weight, and mortality was determined 7 days after infestation. The fungal population in soil, expressed as cfu/g soil, was determined by dilution-plating soil suspensions on to the selective medium of Doberski and Tribe, 1980, Transactions of the British Mycological Society 74, 95–100. The results are shown in Table 4. Since all of the filler/binder mixtures behave in a similar manner, it was concluded that various fillers and binders may be substituted, depending on the physical requirements of the granule. Calflo E, Celite PF and Celite 500 are trade names for powdered filler products obtainable from Celite (UK) Limited, Livington Road, Hassle, North Humberside HU13 OEG.

EXAMPLE 6

Granules were prepared as in Example 5. Nutrients were mixed with the other components of the granule in following proportions: 33% nutrient, 17% biomass, 45% GTY, 5% Fulgel. The following nutrient sources were tested: ground sunflower seed, ground almonds, gram flour, ground textured vegetable protein (TVP), ground barley flakes, ground apple and banana toasted bran cereal, ground rye flour, soya flour, wheatgerm and ground Hijiki seaweed. After drying, the granules were bioassayed against *Diabrotica balteata* as described in Example 3. In pots where granules were added at 1% and 0.5% of soil mass, mortality was determined after 7 days, after 12 days where the granules were added at 0.1%. Fungal propagules were counted at the time of assessment as described in Example 5. The granules were maintained under partial vacuum at ambient laboratory temperatures for 10 months for storage stability studies. The results are shown in Tables 5 and 6.

It is clear from the above results that nutrient sources differ in their effects on efficacy and storage stability of the granules. The nutrient sources which conferred the best combination of efficacy and shelf life were ground sunflower seed, ground almond and soya flour.

EXAMPLE 7

Granules were prepared as described in Example 2. Nutrient sources were added to the mixture before extrusion at a concentration of 33% by weight. The nutrient sources which were tested were ground buckwheat, ground sago, ground aduki beans, ground barley flakes, ground chick peas, ground sunflower seed, ground almond, brown rice flour, carob, fine wheat bran, whole egg replacer and whole wheat semolina. After drying, 1 g of granules was placed between two 5 g layers of soil, adjusted to field capacity, in plastic Universal container. Radial growth and sporulation were assessed through the transparent walls of the container after 31 days of incubation at 20° C. Sporulation was assessed visually according to an arbitrary scale from 0 to 4. Soils from five different sources were used to evaluate the ability of the granules to support fungal growth and sporulation across a range of soil types. The results are shown in Table 7.

It was evident that a nutrient source was necessary in order to achieve growth and sporulation of the fungus in soil. Ground sunflower seed and ground almond were clearly superior in this regard to the other substrates tested.

EXAMPLE 8

Granules were prepared according to the method of Example 5, except that the biomass was grown for four days mixture prior to extrusion was varied as follows. The granules consisted of 17% by weight of biomass, 33% of a nutrient source (soya flour or ground sunflower seed). Other components (PEG 4000 (polyethylene glycol of molecular weight 4000) and the botanical oils soya oil, corn oil or groundnut oil) were added at a concentration of 5%, with the remainder consisting of GTY powder. The granules were stored in a vacuum-sealed desiccator at ambient laboratory temperature for a 12 month period. Viability counts were taken after 0, 1, 4, 8 and 12 months of storage. The results are shown in Table 8.

Granules prepared using ground sunflower seed were more stable during storage than those based on soya flour. The stability of granules based on soya flour could be improved by the addition of sunflower oil at 1%, corn oil, groundnut oil, or PEG.

After 12 months, the granules were bioassayed against *D. balteata* as described in Example 3. Granules were incorporated into soil at 0.5% and 1% by weight, and mortality assessed after 9 and 8 days respectively. The results are shown in Table 9.

It was evident that all of the granules had retained some activity at the end of the 12 month storage period, granules based on ground sunflower seed, soya flour+PEG, and soya flour+groundnut oil being the most active of those tested.

EXAMPLE 9

Granules were prepared as in Example 5, except that the biomass was grown for five days, and the granules consisted of 17% fungal biomass, 33% ground sunflower seed, and 50% GTY/Fulgel. Two large polypropylene fish ponds were filled with unsieved field soil (Wisborough Green silty clay loam), with a layer of grit and washed silver sand placed on the base of the pond to assist drainage. Two furrows, approximately 8 cm wide, 6 cm deep, 90 cm long and 75 cm apart were prepared in each pond. Twenty seeds of sweetcorn (cv. Earliking) were sown in the base of each furrow. Soil removed from the furrows was replaced directly in the case of the untreated pond, or after mixing with 1.93 g of granules per furrow in the case of the treated pond, concentration of granules being greatest in the layer of soil immediately in contact with the seed.

Moisture content was maintained at 15–20% throughout the experiment. At one week after planting, the number of seedlings per row was reduced to 11. At two weeks after planting, five newly hatched larvae of *D. balteata* were added to each of 28 depressions in the soil in each pond. One week later, a further 70 larvae were introduced into the soil as above.

At 38 days after planting, the height of plants was measured, and soil samples removed from each pond. Conidial numbers were determined by exposing the soil samples to a temperature of 60° C. for 18 hours to inactivate hyphae and blastospores. Conidial counts from 14 replicate samples were then determined by dilution plating as described in Example 5. The plants were removed from the soil, and root damage assessed according to a 1–10 scale, 10 being the most severe. After removal of the plants, the soil was covered with polyethylene sheeting in order to contain any adult *D. balteata* beetles which emerged during a 17 day period. These were counted and any symptoms noted. The results are shown in Table 10.

It was evident that, when applied to field soil at commercially acceptable rates, the granules caused the fungus to establish an effective population in the soil, and to maintain this population over a period of several weeks.

EXAMPLE 10

Granules were prepared as in Example 5, with the following modifications. Fungal inoculum was grown for either two or seven days.

Prior to mixing, the biomass was soaked for two hours in deionised water, 6 molar sorbitol, 40% w/v of PEG 4000, or a mixture of mannitol and magnesium chloride (74 g and 27 g respectively per litre deionised water), rinsed four times for a total of 20 minutes in deionised water, and incorporated into granules containing soya flour. Granules without a nutrient source were formulated directly without being exposed to osmoregulants. The granules were sampled after 0, 1, 6 and 12 months of storage under vacuum in a desiccator at ambient laboratory temperature. The results are shown in Table 11.

It may be seen that the poor storage stability which resulted when two day old biomass was formulated with soya flour could be overcome by treating the biomass with osmoregulants prior to formulation, or by delaying the time of harvest.

EXAMPLE 11

Granules were prepared as in Example 5. Before preparation of the granules, subsamples of the soya flour were amended with the preservatives ascorbic acid (0.5%), tocopherol (0.026%) or BHA/BHT (a 1:1 mixture of butylated hydroxyanisole and butylated hydroxytoluene (0.014%)). After drying, the granules were stored either in vacuum-sealed bags or in a desiccator under vacuum in the presence of silica gel. Immediately after preparation, and after six months of storage at laboratory temperature, the granules were bioassayed against Diabrotica balteata as described in Example 3. The granules were added at 0.5% of soil mass, and incubated in soil for three days to allow growth and sporulation to take place before the larvae were added. Mortality was assessed 7 days after infestation. The results are shown in Table 12.

It may be seen that storage stability under suboptimal conditions was enhanced by the addition of the preservative BHA/BHT.

TABLE 1

| Nutrient source | Radial growth (mm) | Sporulation |
|---|---|---|
| None | 0 | — |
| Oatmeal | 1–2 | +++ |
| Soya flour | 6–8 | ++++ |
| Wheatgerm | 1 | +++ |
| Coarse cornmeal | 4 | ++ |
| Fine cornmeal | 0.25 | + |
| Skim milk powder | 1 | +++ |

TABLE 2

| | MORTALITY OF Diabrotica balteata (%) | | | | D. virgifera (%) | |
|---|---|---|---|---|---|---|
| | Application rate 1% | | 3% | | 1% | |
| Granule | − soya | + soya | − soya | + soya | − soya | + soya |
| Hy 17% | 10 | 96 | 31 | 100 | 35 | 88 |
| Hy 10% | 11 | 80 | 9 | 100 | 20 | 68 |
| Hy 1.7% | 14 | 49 | 33 | 100 | 25 | 38 |
| Bs 17% | 8 | 88 | 29 | 100 | 25 | 68 |
| Bs 10% | 19 | 100 | 16 | 100 | 25 | 93 |
| Bs 1.7% | 13 | 46 | 9 | 91 | 25 | 45 |
| Control | | 11 | | | | 30 |

TABLE 3

| Drying regime and | Moisture | Viability (cfu/g) after storage | | | |
|---|---|---|---|---|---|
| culture age | content | 4 days | 31 days | 6 months | 12 mos. |
| Undried, 7 days | 28.2% | $3 \times 10^8$ | $4 \times 10^7$ | $9 \times 10^2$ | $1 \times 10^3$ |
| Undried, 4 days | 28.6% | $2 \times 10^8$ | $5 \times 10^6$ | $7 \times 10^5$ | $6 \times 10^2$ |
| Dried, 7 days | 12.1% | $2 \times 10^8$ | $2 \times 10^8$ | $1 \times 10^5$ | $5 \times 10^4$ |
| Dried, 4 days | 11.6% | $1 \times 10^8$ | $8 \times 10^7$ | $6 \times 10^2$ | $6 \times 10^2$ |
| Dried, 7 days | 6.5% | $3 \times 10^8$ | $3 \times 10^8$ | $2 \times 10^7$ | $3 \times 10^7$ |
| Dried, 4 days | 5.4% | $2 \times 10^8$ | $6 \times 10^7$ | $1 \times 10^7$ | $1 \times 10^7$ |
| Dried, 7 days | 2.5% | $2 \times 10^8$ | $1 \times 10^8$ | $4 \times 10^7$ | $4 \times 10^7$ |
| Dried, 4 days | 2.1% | $1 \times 10^8$ | $7 \times 10^7$ | $1 \times 10^6$ | $1 \times 10^5$ |

TABLE 4

Mortality of Diabrotica balteata (cfu/g soil)

| | BINDER | | | |
|---|---|---|---|---|
| FILLER | None | Fulgel | Borrebond | PEG 4000 |
| GTY | 88% | 88% | 98% | 73% |
| | $(1 \times 10^7)$ | $(6 \times 10^6)$ | $(1 \times 10^6)$ | $(7 \times 10^5)$ |
| Calflo E | 100% | 83% | 93% | 98% |
| | $(6 \times 10^4)$ | $(3 \times 10^7)$ | $(4 \times 10^5)$ | $(5 \times 10^5)$ |
| Celite PF | 100% | 95% | 75% | 90% |
| | $(8 \times 10^6)$ | $(6 \times 10^6)$ | $(3 \times 10^6)$ | $(7 \times 10^6)$ |
| Celite 500 | 98% | 95% | 58% | 75% |
| | $(2 \times 10^6)$ | $(8 \times 10^5)$ | $(1 \times 10^5)$ | $(2 \times 10^6)$ |

Control mortality 8%

TABLE 5

| | Mortality of D. balteata and (cfu/g soil) | | |
|---|---|---|---|
| | 1.0% (7 days) | 0.5% (7 days) | 0.1% (½ days) |
| Ground sunflower seed | 95% $(2 \times 10^6)$ | 58% $(3 \times 10^5)$ | 60% $(2 \times 10^5)$ |
| Ground almond | 98% $(4 \times 10^5)$ | 65% $(9 \times 10^5)$ | 78% $(3 \times 10^4)$ |
| Gram flour | 38% $(8 \times 10^3)$ | 33% $(<2 \times 10^3)$ | 30% $(5 \times 10^3)$ |
| Ground TVP | 73% $(1 \times 10^4)$ | 30% $(3 \times 10^4)$ | 28% $(1 \times 10^3)$ |
| Barley flakes | 83% $(1 \times 10^5)$ | 30% $(3 \times 10^5)$ | 38% $(9 \times 10^3)$ |
| Ground toasted cereal | 53% $(2 \times 10^4)$ | 20% $(2 \times 10^3)$ | 25% $(4 \times 10^3)$ |
| Rye flour | 25% $(4 \times 10^4)$ | 33% $(4 \times 10^3)$ | 10% $(1 \times 10^4)$ |
| Soya flour | 95% $(1 \times 10^5)$ | 90% $(2 \times 10^5)$ | 33% $(3 \times 10^5)$ |
| Wheatgerm | 53% $(8 \times 10^3)$ | 38% $(2 \times 10^5)$ | 20% $(2 \times 10^3)$ |
| Hijiki seaweed | 18% $(<2 \times 10^3)$ | 10% $(<2 \times 10^3)$ | 33% $(<2 \times 10^3)$ |

TABLE 6

| | Viability (cfu/g granules) after storage | | |
|---|---|---|---|
| | 0 months | 1 month | 10 months |
| Ground sunflower seed | $7 \times 10^6$ | $7 \times 10^6$ | $3 \times 10^6$ |
| Ground almond | $1 \times 10^7$ | $6 \times 10^6$ | $6 \times 10^6$ |
| Gram flour | $6 \times 10^5$ | $7 \times 10^5$ | $2 \times 10^5$ |
| Ground TVP | $9 \times 10^6$ | $3 \times 10^6$ | $5 \times 10^5$ |
| Ground barley flakes | $2 \times 10^6$ | $3 \times 10^6$ | $3 \times 10^6$ |
| Ground toasted cereal | $1 \times 10^7$ | $6 \times 10^6$ | $8 \times 10^5$ |
| Rye flour | $4 \times 10^6$ | $2 \times 10^6$ | $1 \times 10^6$ |
| Soya flour | $3 \times 10^7$ | $1 \times 10^7$ | $3 \times 10^6$ |
| Wheatgerm | $3 \times 10^6$ | $3 \times 10^6$ | $9 \times 10^5$ |
| Hijiki seaweed | $3 \times 10^6$ | $9 \times 10^5$ | $1 \times 10^5$ |

TABLE 7

| | Soil | | | | | | | | | |
|---|---|---|---|---|---|---|---|---|---|---|
| | Champ. | | PTM | | EA | | Penf. | | Peat | |
| Nutrient source | RG | Sp | RG | Sp | RG | Sp | RG | Sp | RG | Sp |
| None | 0 | 1 | 0 | 1 | 0 | 1 | 0 | 1 | 0 | 1 |
| Buckwheat | 1 | 2 | 5 | 1 | 1 | 1 | 2 | 2 | 2 | 1 |
| Sago | 0.5 | 1 | 0.5 | 1 | 0.5 | 1 | 0.5 | 1 | 3 | 1 |
| Aduki bean | 1 | 1 | 1 | 1 | 2 | 1 | 1 | 2 | 2 | 2 |
| Barley flakes | 3 | 1 | 3 | 1 | 5 | 2 | 3 | 2 | 4 | 3 |
| Chick peas | 1 | 1 | 2 | 1 | 1 | 2 | 3 | 2 | 2 | 2 |
| Sunflower seed | 10 | 4 | 8 | 4 | 9 | 4 | 5 | 2 | 10 | 3 |
| Almond | 8 | 4 | 7 | 4 | 10 | 3 | 8 | 3 | 9 | 2 |

TABLE 7-continued

| | Soil | | | | | | | | | |
|---|---|---|---|---|---|---|---|---|---|---|
| | Champ. | | PTM | | EA | | Penf. | | Peat | |
| Nutrient source | RG | Sp | RG | Sp | RG | Sp | RG | Sp | RG | Sp |
| Brown rice flour | 1 | 1 | 1 | 1 | 1 | 1 | 1 | 1 | 2 | 1 |
| Carob | 1 | 1 | 1 | 0 | 1 | 1 | 1 | 1 | 1 | 2 |
| Fine wheat bran | 1 | 2 | 2 | 1 | 2 | 2 | 2 | 1 | 1 | 2 |
| Egg replacer | 1 | 1 | 1 | 1 | 1 | 1 | 1 | 1 | 5 | 3 |
| Semolina | 1 | 1 | 4 | 1 | 1 | 2 | 1 | 1 | 4 | 1 |

Champ. = Silty clay loam, Champaign, IL, USA
PTM = Sandy loam, Pear Tree Meadow, Jealott's Hill, Berkshire, UK
EA = Loamy sand, East Anglia Field Station, Mildenhall, Suffolk, UK
Penf. = Sandy loam, Penfurzen Field, Jealott's Hill, Berkshire, UK
Peat = commercial peat compost
RG = radial growth (mm)
Sp. = sporulation
0 = o sporulation, 4 = heavy sporulation

TABLE 8

| | Viability (cfu/g granule) during storage MONTH | | | | |
|---|---|---|---|---|---|
| Nutrient source | 0 | 1 | 4 | 8 | 12 |
| Soya | $5 \times 10^8$ | $6 \times 10^8$ | $3 \times 10^8$ | $2 \times 10^7$ | $3 \times 10^7$ |
| Sunflower seed | $6 \times 10^8$ | $8 \times 10^8$ | $1 \times 10^8$ | $6 \times 10^8$ | $2 \times 10^8$ |
| Soya + 1% sunflower oil | $3 \times 10^8$ | $3 \times 10^8$ | $3 \times 10^8$ | $6 \times 10^7$ | $1 \times 10^8$ |
| Soya + 5% sunflower oil | $3 \times 10^8$ | $3 \times 10^8$ | $6 \times 10^7$ | $3 \times 10^7$ | $2 \times 10^7$ |
| Soya + PEG | $5 \times 10^8$ | $4 \times 10^8$ | $2 \times 10^8$ | $2 \times 10^7$ | $8 \times 10^7$ |
| Soya + PEG + 5% sunfl. oil | $3 \times 10^8$ | $1 \times 10^8$ | $4 \times 10^7$ | $7 \times 10^7$ | $7 \times 10^7$ |
| Soya + 1% corn oil | $4 \times 10^8$ | $4 \times 10^8$ | $5 \times 10^7$ | $6 \times 10^7$ | $6 \times 10^7$ |
| Soya + 5% corn oil | $4 \times 10^8$ | $3 \times 10^8$ | $7 \times 10^7$ | $6 \times 10^7$ | $6 \times 10^7$ |
| Soya + 1% groundnut oil | $3 \times 10^8$ | $4 \times 10^8$ | $1 \times 10^8$ | $8 \times 10^7$ | $8 \times 10^7$ |
| Soya + 1% groundnut oil | $9 \times 10^8$ | $4 \times 10^8$ | $1 \times 10^8$ | $1 \times 10^8$ | $2 \times 10^8$ |

TABLE 9

| Nutrient source | Mortality after 9 days, 0.5% granules | Mortality after 8 days, 1.0% granules |
|---|---|---|
| Soya | 23% | 13% |
| Sunflower seed | 63% | 89% |
| Soya + 1% sunflower oil | 18% | 19% |
| Soya + 5% sunflower oil | 18% | 19% |
| Soya + PEG | 25% | 49% |
| Soya + PEG + 5% sunfl. oil | 10% | 15% |
| Soya + 1% corn oil | 25% | 35% |
| Soya + 5% corn oil | 30% | 31% |
| Soya + 1% groundnut oil | 25% | 36% |
| Soya + 1% groundnut oil | 30% | 58% |

Control mortality (0.5% incorporation) = 0%
Control mortality (1.0% incorporation) = 5%

TABLE 10

| | Untreated | Granules applied |
|---|---|---|
| Mean plant height | 50 cm | 35 cm |
| Conidial population | Undetectable | $3.0 \times 10^6$ cfu/g soil |
| Root damage (1–10) | 7.8 | 3.5 |
| Live adults per pond | 34 | 1 (mycosed after 2 d) |

TABLE 11

| Nutrient source, osmoregulant | Viability (cfu/g granule) after storage | | | |
|---|---|---|---|---|
| treatment and age of culture | 0 months | 1 month | 6 months | 12 mos. |
| No nutrient, 2 days | $3 \times 10^8$ | $2 \times 10^8$ | $8 \times 10^7$ | $2 \times 10^7$ |
| Soya flour, water, 2 days | $6 \times 10^8$ | $5 \times 10^8$ | $1 \times 10^7$ | $5 \times 10^5$ |
| Soya flour, sorbitol, 2 days | $3 \times 10^8$ | $3 \times 10^8$ | $1 \times 10^8$ | $1 \times 10^7$ |
| Soya flour, PEG, 2 days | $5 \times 10^8$ | $9 \times 10^8$ | $1 \times 10^8$ | $1 \times 10^7$ |
| Soya flour, mannitol/MgCl$_2$, 2 d | $5 \times 10^8$ | $4 \times 10^8$ | $1 \times 10^8$ | $2 \times 10^6$ |
| No nutrient, 7 days | $5 \times 10^8$ | $1 \times 10^9$ | $5 \times 10^8$ | $5 \times 10^8$ |
| Soya flour, water, 7 days | $7 \times 10^8$ | $2 \times 10^9$ | $6 \times 10^8$ | $1 \times 10^8$ |
| Soya flour, sorbitol, 7 days | $9 \times 10^8$ | $1 \times 10^9$ | $5 \times 10^8$ | $2 \times 10^8$ |
| Soya flour, PEG, 7 days | $1 \times 10^9$ | $8 \times 10^8$ | $2 \times 10^8$ | $5 \times 10^7$ |
| Soya flour, mannitol/MgCl$_2$, 7 d | $7 \times 10^8$ | $9 \times 10^8$ | $6 \times 10^8$ | $2 \times 10^8$ |

TABLE 12

| | Mortality of D. balteata after 7 days | | |
|---|---|---|---|
| Preservative | 0 months | 6 months, desiccator | 6 months, vacuum sealed bags |
| None | 87% | 64% | 24% |
| Ascorbic acid | 72% | 69% | 24% |
| Tocopherol | 79% | 76% | 18% |
| BHA/BHT | 73% | 78% | 60% |

Control mortality 8% at 0 months, 6% at six months

We claim:

1. A method of controlling soil-dwelling insect pests which comprises applying to the soil where the pests are present or are expected to be present, an extruded granular composition comprising a pesticidally effective amount of a fungal biological control agent in the form of blastospores, wherein the fungal biological control agent is an enlomopathogen selected from the genera Beauveria, Verticillium, Nomuraea, Hirsutelela, Tolypocladiuin, Paecilomyces and Metarhizium, and a complex nutrient source in an amount sufficient to achieve growth and sporulation of the fungus after application of said composition to soil or to plant surfaces.

2. The method of claim 1 wherein the entomopathogen is *Beauveria bassiana*.

3. The method of claim 1 wherein the pests are Diabrotica spp.

* * * * *